(12) United States Patent
Cruz et al.

(10) Patent No.: US 8,182,440 B2
(45) Date of Patent: May 22, 2012

(54) DIALYSIS MACHINE HAVING COMBINATION DISPLAY AND HANDLE

(75) Inventors: Edward Cruz, Newbury Park, CA (US); John K. Clay, Topanga, CA (US); Mark Westcott, Grand Terrace, CA (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 1946 days.

(21) Appl. No.: 10/256,355

(22) Filed: Sep. 27, 2002

(65) Prior Publication Data

US 2004/0064080 A1 Apr. 1, 2004

(51) Int. Cl.
*A61M 37/00* (2006.01)
*C02F 1/44* (2006.01)

(52) U.S. Cl. .................. 604/4.01; 604/5.01; 604/5.04; 604/6.09; 210/646

(58) Field of Classification Search ............... 604/4.01, 604/5.01, 5.04, 6.05, 6.09, 6.16, 6.06, 6.1, 604/264, 6.11, 6.13–6.14; 210/143, 645, 210/646, 195.2; 345/905; 422/44, 48, 243; 312/209

See application file for complete search history.

(56) References Cited

U.S. PATENT DOCUMENTS

| | | | |
|---|---|---|---|
| 2,969,150 A | 1/1961 | Broman | |
| 5,514,335 A | 5/1996 | Leonard et al. | |
| 5,629,871 A * | 5/1997 | Love et al. .................. 702/34 |
| 5,650,071 A | 7/1997 | Brugger et al. | |
| D383,842 S | 9/1997 | Kenley et al. | |
| 5,679,245 A * | 10/1997 | Manica .................... 210/134 |
| D389,916 S | 1/1998 | DiPerna et al. | |
| D395,085 S | 6/1998 | Kenley et al. | |
| 5,762,805 A | 6/1998 | Truitt et al. | |
| D396,289 S | 7/1998 | McGugan | |
| 5,776,091 A | 7/1998 | Brugger et al. | |
| 5,776,345 A | 7/1998 | Truitt et al. | |
| 5,782,796 A | 7/1998 | Din et al. | |
| 5,788,851 A | 8/1998 | Kenley et al. | |
| D399,960 S | 10/1998 | Prokop et al. | |
| D402,369 S | 12/1998 | Prokop et al. | |
| 5,868,710 A | 2/1999 | Battiato et al. | |
| D406,893 S | 3/1999 | Menhennett et al. | |
| D406,894 S | 3/1999 | Menhennett et al. | |

(Continued)

FOREIGN PATENT DOCUMENTS

EP 0 987 036 A2 3/2000

(Continued)

OTHER PUBLICATIONS

Foreign associate report of Office Action from Mexican Patent Appl. No. PA/a/2005/002130, dated Apr. 22, 2008.

*Primary Examiner* — Leslie Deak
(74) *Attorney, Agent, or Firm* — K&L Gates LLP

(57) ABSTRACT

The present invention provides a dialysis machine that is readily moved by a patient, nurse or other operator. A display is provided on the front of the machine, which displays and controls various dialysis functions. The display is robust, mounted directly to the body and includes an open area that can be grasped by a person to move the entire machine. The combination display/handle enables the person to move the machine from the front of same and from odd angles with respect to the machine.

20 Claims, 6 Drawing Sheets

U.S. PATENT DOCUMENTS

| | | |
|---|---|---|
| 5,910,252 A | 6/1999 | Truitt et al. |
| 5,924,781 A | 7/1999 | Mitchell |
| 5,925,022 A | 7/1999 | Battiato et al. |
| D412,578 S | 8/1999 | Andersson et al. |
| 6,004,292 A | 12/1999 | Battiato et al. |
| D420,444 S | 2/2000 | McGugan |
| 6,086,576 A | 7/2000 | Bisch |
| 6,117,122 A | 9/2000 | Din et al. |
| 6,143,181 A * | 11/2000 | Falkvall et al. ............... 210/646 |
| 6,146,523 A * | 11/2000 | Kenley et al. ................. 210/143 |
| D446,860 S | 8/2001 | Mezière et al. |
| D446,861 S | 8/2001 | Mezière et al. |
| 6,613,280 B2 * | 9/2003 | Myrick et al. .................. 422/45 |
| 6,626,445 B2 * | 9/2003 | Murphy et al. ............ 280/47.34 |
| 6,796,955 B2 * | 9/2004 | O'Mahony et al. .......... 604/6.11 |

FOREIGN PATENT DOCUMENTS

| | | |
|---|---|---|
| EP | 0987036 | 3/2000 |
| JP | 05-176991 | 7/1993 |
| JP | 06-315530 | 11/1994 |
| WO | 96/24396 | 8/1996 |
| WO | 96/40320 | 12/1996 |
| WO | 98/22168 | 5/1998 |
| WO | 00/41746 | 7/2000 |
| WO | 01/36022 | 5/2001 |
| WO | 02/26286 | 4/2002 |
| WO | WO02/26286 A3 | 4/2002 |

* cited by examiner

DIALYSIS MACHINE HAVING COMBINATION DISPLAY AND HANDLE

BACKGROUND OF THE INVENTION

This invention generally relates to the field of medical devices. More particularly the present invention relates to hemodialysis machines having a graphical user interface.

It is known to provide dialysis to treat kidney failure. To this end, different methods of providing dialysis have been developed.

One type of dialysis is hemodialysis, which removes waste from a patient's blood. Hemodialysis is performed using machines that typically include an extracorporeal blood circuit. The blood circuit includes an arterial line, a blood pump, a dialyzer and a venous line. The patient is connected to the arterial and venous lines via a catheter inserted into the patient's vein or artery. The blood pump removes blood from the patient and pumps same through the arterial line to an inlet or blood side of the membrane in the dialyzer. The dialyzer typically includes a semipermeable membrane that separates waste components, such as toxins and excess water from the patient's blood.

A separate pump is provided that pumps dialysate through a dialysate side of the membrane of the dialyzer. The waste components flow from the blood across the membrane to the dialysate. A large amount of dialysate, for example about one hundred twenty liters, is used to dialyze the blood during a single hemodialysis therapy. The membrane is designed to prevent waste components from flowing from the dialysate back to the patient's blood. The blood pump returns the blood from the dialyzer to the patient via the venous line. The spent dialysate is then discarded. Hemodialysis treatment lasts several hours and is generally performed in a treatment center about three or four times per week.

Another type of dialysis is peritoneal dialysis. Peritoneal dialysis is preformed using a device that pumps dialysate into a patient's peritoneal cavity, which is infused through a catheter implanted in the cavity. The dialysate contacts the patient's peritoneal membrane in the peritoneal cavity. Waste, toxins and excess water pass from the patient's bloodstream through the peritoneal membrane and into the dialysate due to diffusion and osmosis, i.e., an osmotic gradient that occurs across the membrane. The spent dialysate drains from the patient's peritoneal cavity, removing the waste, toxins and excess water from the patient. This cycle is repeated.

Dialysis machines generally have controls that regulate the operation of the machine. Older machines used electromechanical buttons and switches to control valves, pump motors, etc., and mechanical gauges to display therapy parameters, such as temperature, pressure, flowrate, etc. These controls are labor intensive and prone, due to their mechanical nature, to inaccuracy and failure.

Newer dialysis machines have used a video monitor to display therapy parameters. Certain machines combine the video monitor with a touch screen so that the inputs and therapy displays are provided on a single display or graphical user interface ("GUI"). Some GUI's also incorporate mechanical or hard keys for redundancy or for simplicity. GUI's enable the patient, nurse or other operator to interact with the machine and adjust machine operation or treatment parameters, e.g., pump rates, dialysate and blood temperature, flow rate, pressure, etc.

Modem GUI's include a host microprocessor that controls the operation of the major components of the machine. When the patient or nurse wishes to change a treatment parameter, the person touches a symbol on the GUI corresponding to the parameter, wherein a menu, for example, is provided to scroll up or down or to key in a value. A verification step can be provided, wherein the patient or nurse confirms the parameter change.

Because the GUI is the focus of attention for a dialysis machine, its location, ease of use, reliability and durability are paramount to the success of the machine and to providing proper therapy. A constant struggle exists between providing multiple options to the user through software improvements and keeping the machine simple to use for both patients, caregivers, nurses and other persons.

One problem with displays both old and new is that they are visible and usable from only one position, typically the front of the machine. Devices have been provided that allow the displays to be rotated and moved in multiple directions. These systems are labor intensive and typically require loosening and fastening a locking mechanism to move the display. While this type of system is operable by a person with two hands free and positioned in front of the machine, a patient lying in a bed or a nurse with one hand busy may find adjusting a locking mechanism and articulating the display to be cumbersome.

A need therefore exists for an improved dialysis machine that enables the display to be easily moved and positioned.

SUMMARY OF THE INVENTION

The present invention provides an improved dialysis machine. As used herein, "dialysis machine" refers to machines that can provide dialysis to a patient including hemodialysis machines, peritoneal dialysis machines and hemofiltration machines and combinations thereof. The dialysis machine houses the various components needed to perform the type of dialysis for which the machine has been designed. For example, the machine includes at least one pump for pumping blood and/or dialysate. The machine includes a number of tubes for transferring either blood to or from a patient's body or dialysate to a dialyzer or to the patient's peritoneal cavity.

The dialysis machine includes one or more devices that enable the machine to be readily moved. In an embodiment, the machine is coupled to a plurality of rollers. The rollers are mounted to the body of the machine. The machine can also include a base that extends from the body wherein one or more of the rollers couples to the base, so as to provide a wider footprint and a more stable foundation for the moveable dialysis machine. The dialysis machine in an embodiment therefore rolls upon being pushed or pulled by a patient, nurse or other operator. The base can also have channels or other contours that funnel fluid that spills onto the base to a location wherein the fluid can be readily cleaned from the machine.

The body of the machine defines at least one cavity that houses a functional component for dialysis therapy. For example, the body can define a cavity housing tubing bulkheads that orient the tubes in a desired direction so that they are biased to extend from the device in a desired direction. A cavity can be provided for holding containers of dialysate or other types of fluids necessary to perform the specified type of dialysis. Further, one or more arms extends from the body of the machine, wherein the arm can for example clutch and grasp, hold or support a container or other type of item.

The body includes multiple panels that provide multiple accessways to the interior of the body. The machine further includes at least one handle attached to the body that enables a patient or nurse to grasp and move the machine. In an embodiment, a handle attaches to both sides of the body and extends towards the back of the machine, providing a rigid and strong handle.

A display or graphical user interface ("GUI") extends outward from the front of the body of the machine. The display includes a video monitor that displays various parameters of the therapy, such as the portion of the therapy that is currently being provided, the amount of solution provided or any other type of therapy parameter. The display further includes one or more electromechanical buttons, dials, knobs or other type of electromechanical input device. The display also includes an open area that does not have any control apparatus. This area is suitable for being grasped, pushed/pulled and moved by a patient or nurse. The display is mounted directly to the body via a mount that is sturdy and rigid enough to enable the patient or nurse to move the machine by moving the display. The display of the present invention therefore also acts as a handle.

The display also includes a chart holder, which in an embodiment is a bent wire or thin metal or plastic rod that extends from the back of the display. A lower portion of the back of the display, below the chart holder, couples directly to the front of the body.

The combination handle and display provides a number of advantages. One advantage provided by the combination display and handle of the present invention is that the dialysis machine can be moved without having to walk behind the machine and push the machine so that the display is in a desired location.

Another advantage of the combination display and handle of the present invention is that it enables a patient lying in bed to grasp and move the machine while being at an odd angle with respect to the machine.

A further advantage of the combination handle and display is that it provides a display that is robust and not prone to being damaged due to contact by the patient or nurse.

Additional features and advantages of the present invention are described in, and will be apparent from, the following Detailed Description of the Invention and the figures.

DETAILED DESCRIPTION OF THE INVENTION

Figure 1:
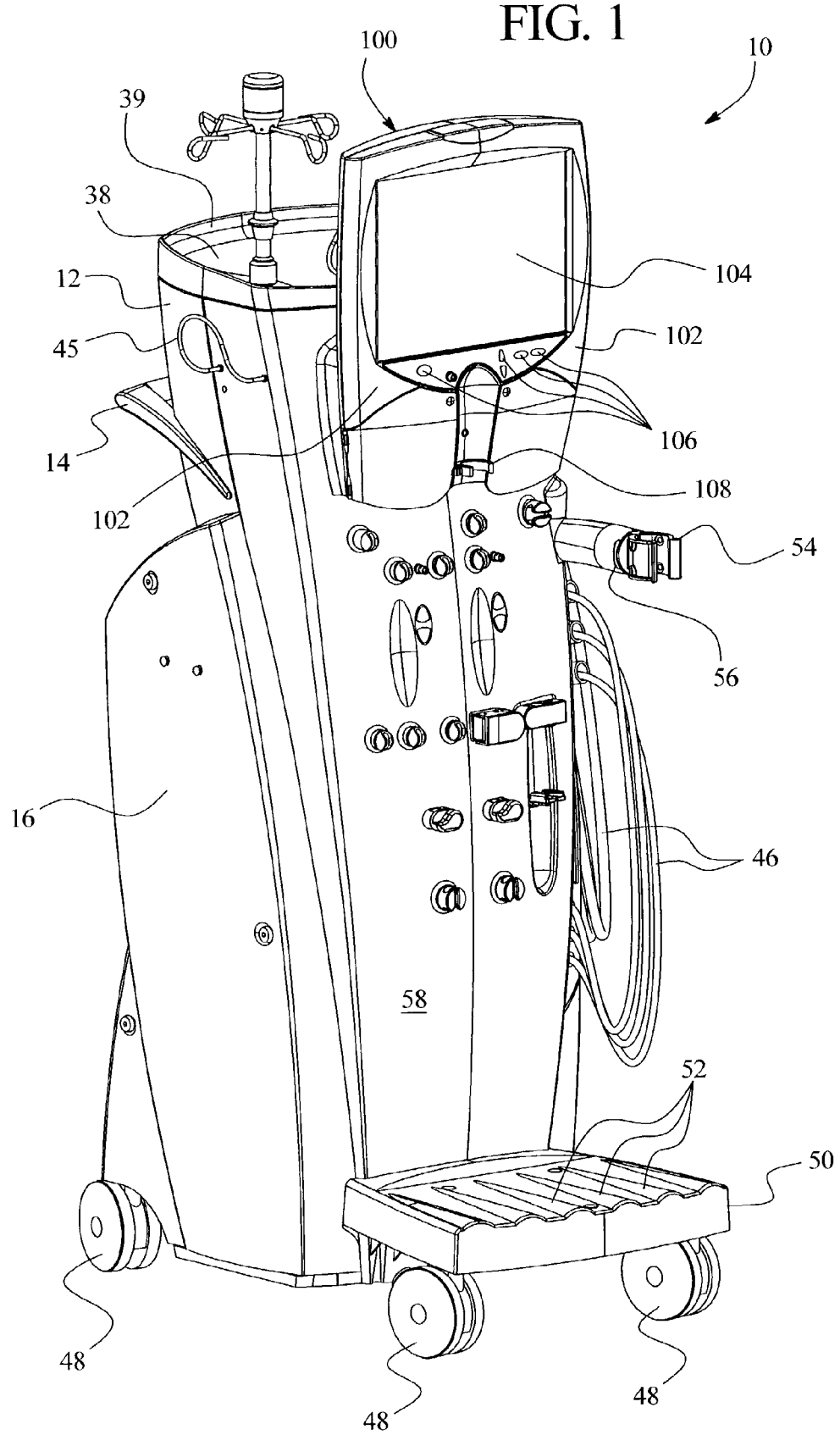
FIG. 1 illustrates a top, front and right side perspective view of an embodiment of a hemodialysis machine incorporating the combination display and handle of the present invention.

Referring now to the drawings, FIGS. 1 to 6 illustrate various views of a hemodialysis machine 10, which includes a body 12 and combination display and handle 100. Although a hemodialysis machine is illustrated, the present invention as noted above is not limited to use in a hemodialysis procedure or device. A handle 14 is additionally provided, which is attached to the sides of the body 12 as best seen in FIGS. 1, 2, 4, 5 and 6. Mounting the handle 14 to the sides of the body 12 provides rigidity and strength not only to the handle 14 but to the overall feel when moving dialysis machine 10 via handle 14. Handle 14 is molded and contoured to provide a comfortable feel for a caregiver grabbing same and is oriented slightly upward to provide easier manipulation of machine 10.

Figure 2:
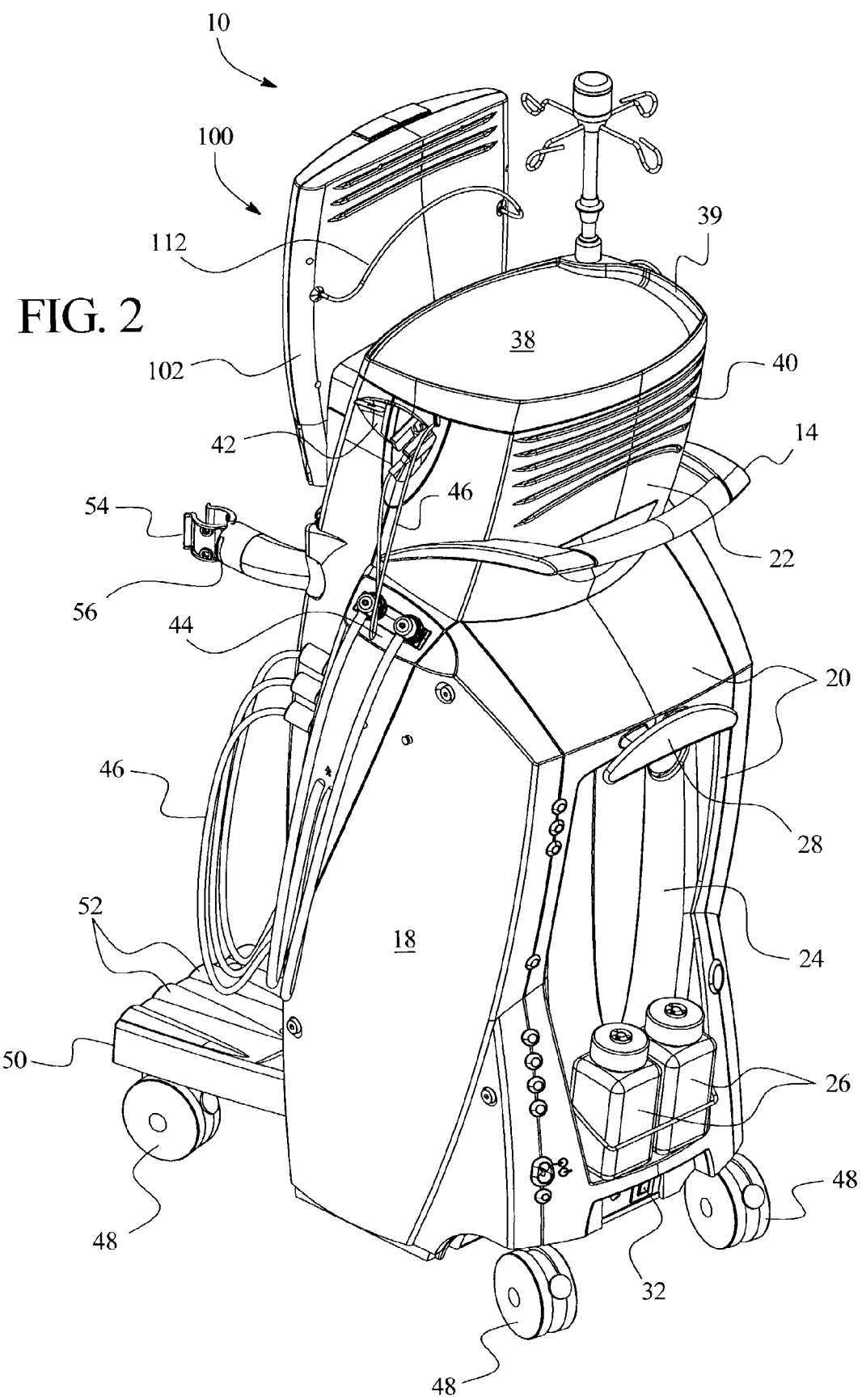
FIG. 2 illustrates a top, rear and left side perspective view thereof.
Figure 3:
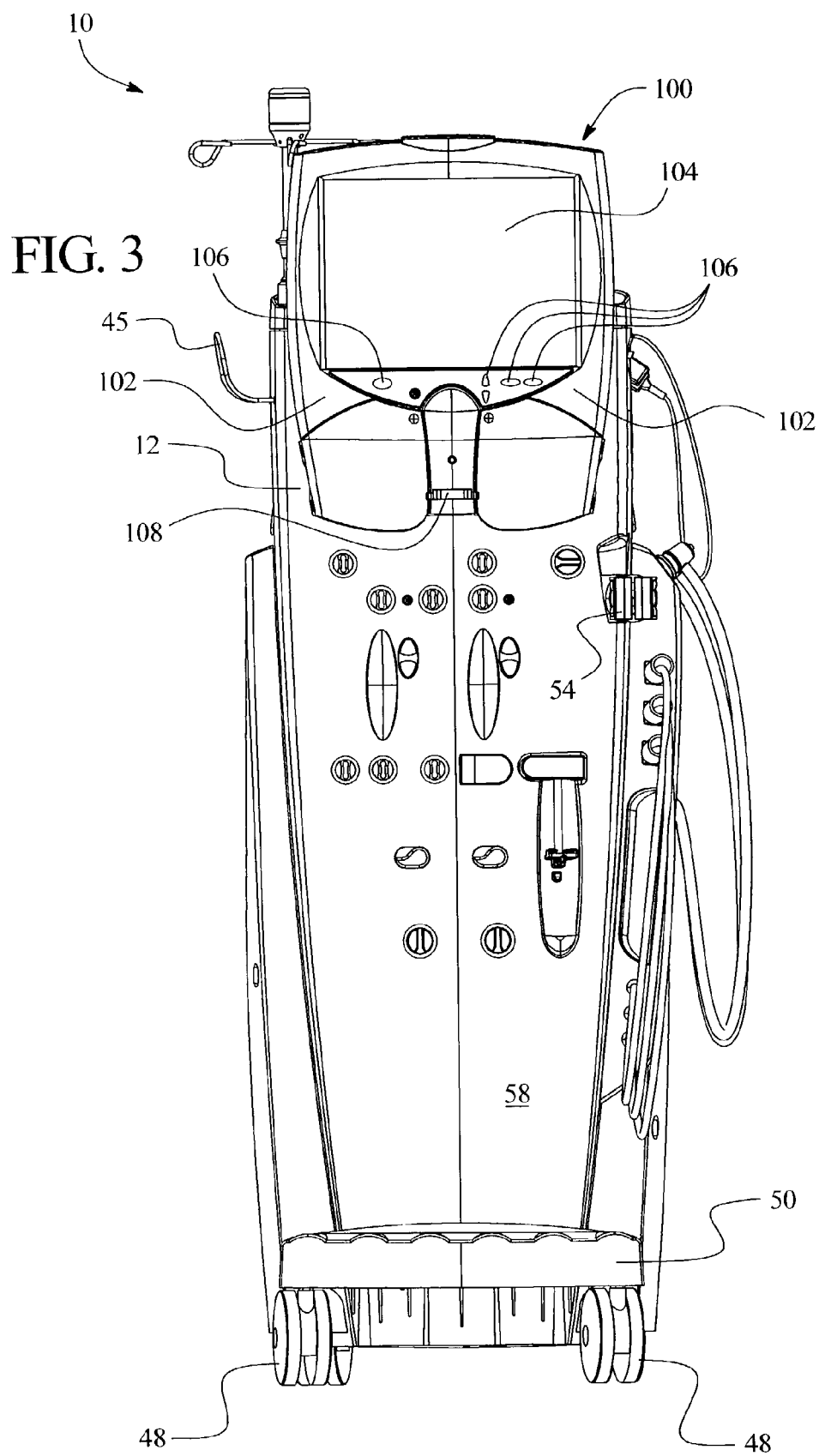
FIG. 3 illustrates a front view thereof.
Figure 4:
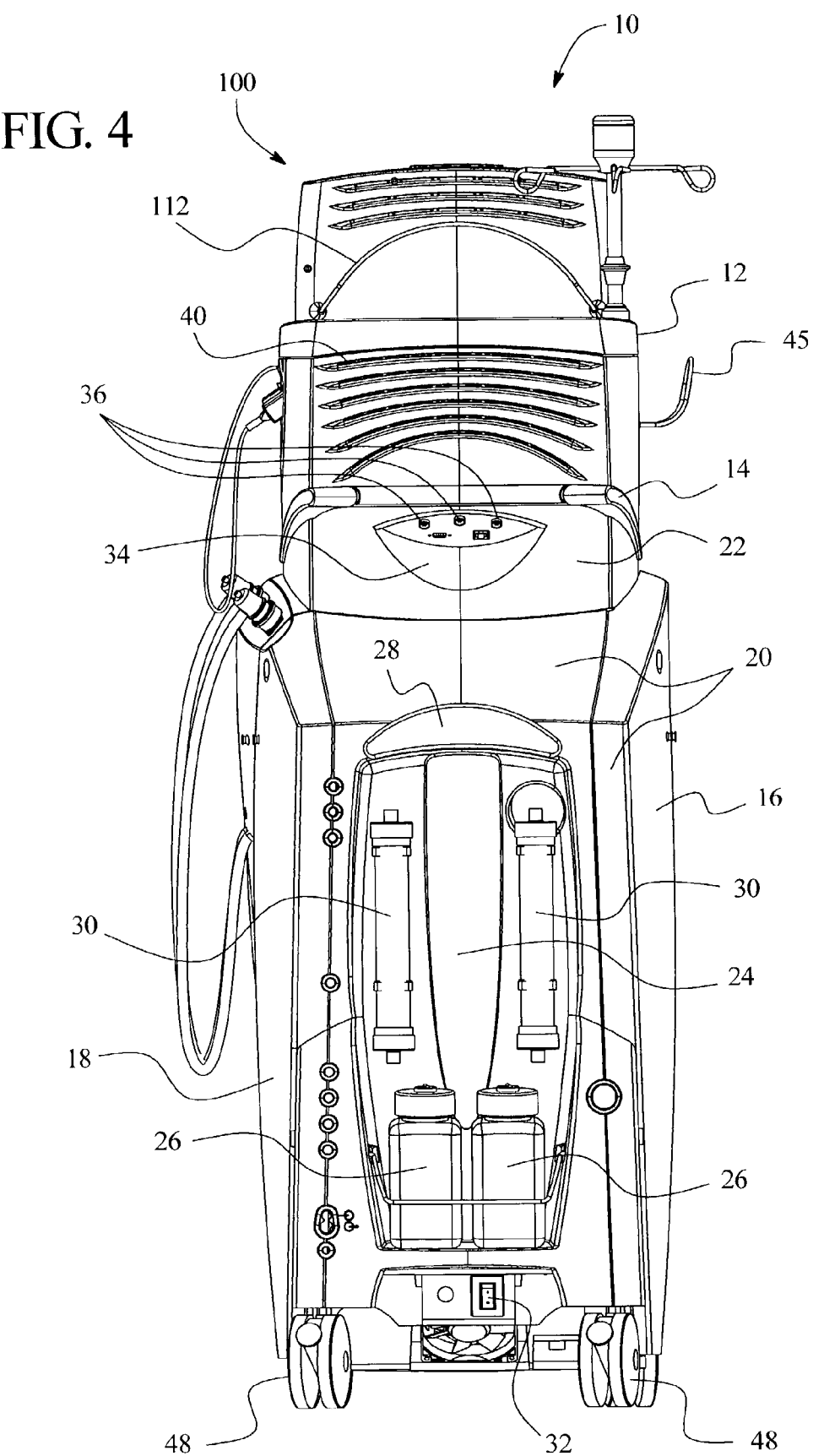
FIG. 4 illustrates a rear view thereof.
Figure 5:
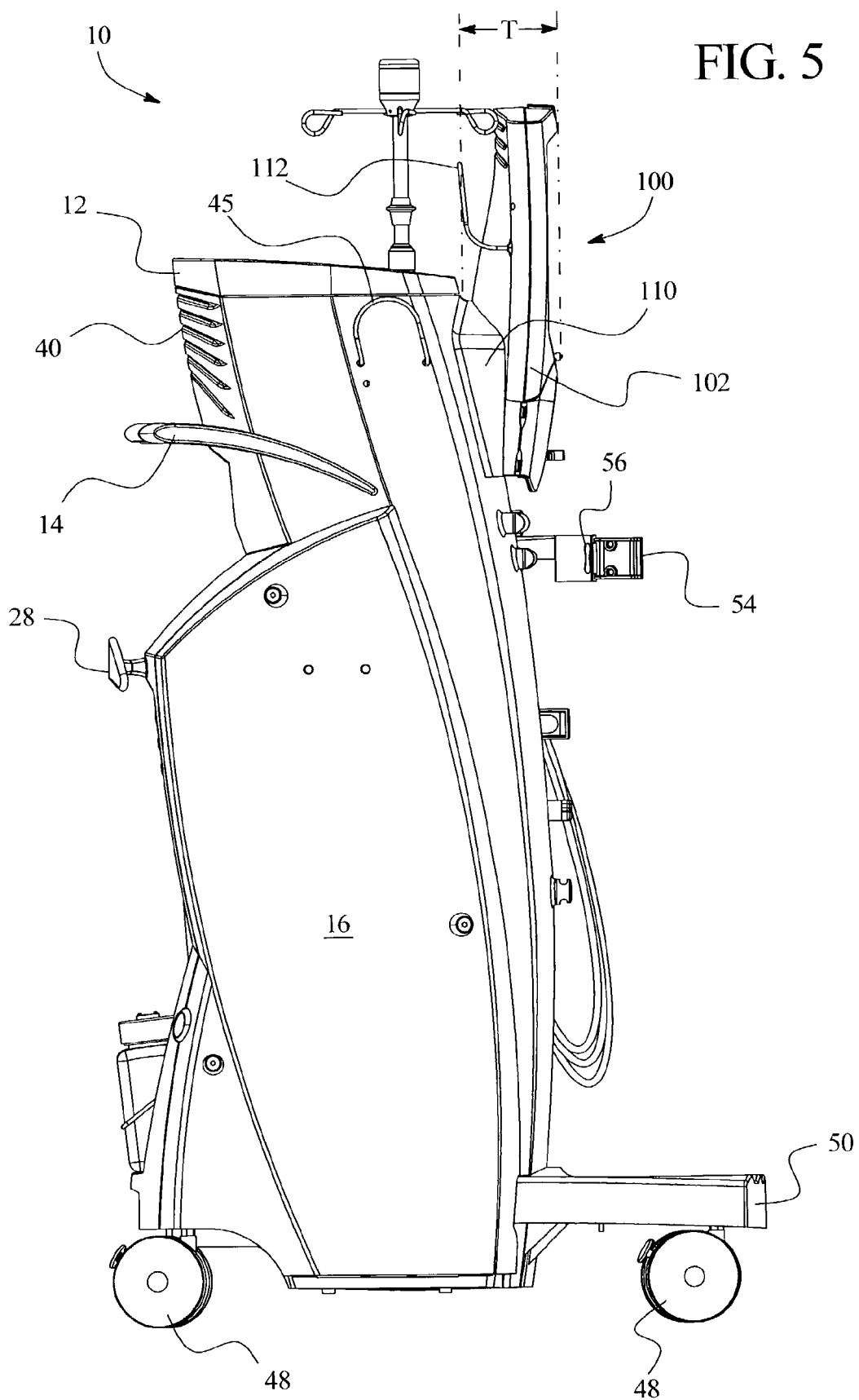
FIG. 5 illustrates a right side view thereof.
Figure 6:
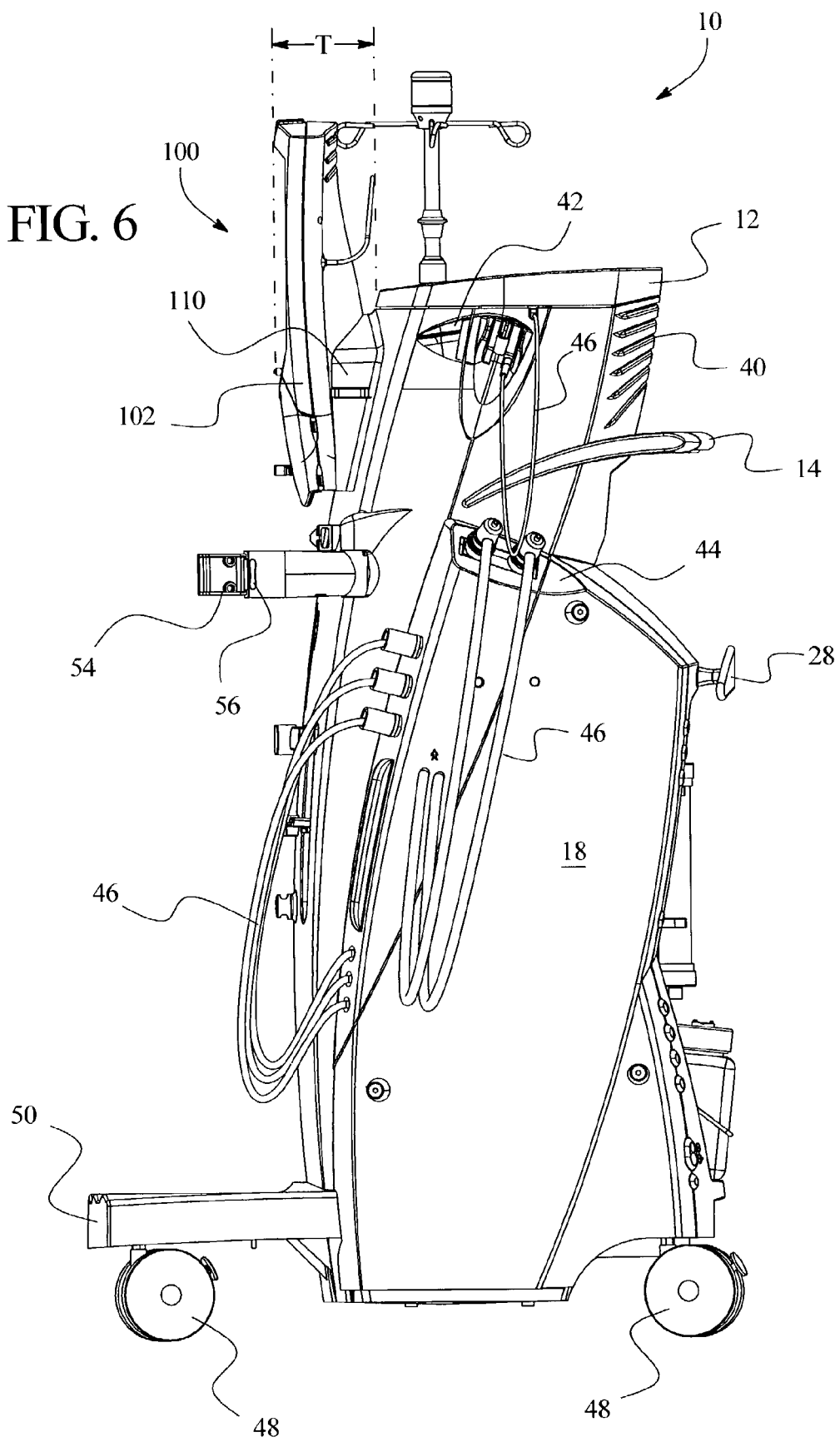
FIG. 6 illustrates a left side view thereof.

The body 12 includes multiple accessways into the interior of the machine 10. FIGS. 1, 4 and 5 show a right side access panel 16. FIGS. 2, 4 and 6 illustrate a left side access panel 18. Panels 16 and 18 are either hingedly openable or completely removeable to allow access to the front fluidix and the lower electronics inside body 12 of machine 10. The fluidix include the devices described above for the extracorporeal blood circuits, including the arterial line, the blood pump, the dialyzer and the venus line in a hemodialysis device, and a cycler cassette, pumps, valves, infusion line and drain line for peritoneal dialysis. FIGS. 2 and 4 illustrate a lower back side access panel 20 that is completely removable or hingedly openable to allow access to the back fluidix. FIGS. 2 and 4 also illustrate a removable or hinged upper back side access panel 22 that allows access to the upper electronics. The lower back side access panel 20 also defines a cavity 24 that holds a number of containers 26 of solution, such as a disinfectant, or any other type of solution necessary for the dialysis therapy.

A cleat 28 is attached to the lower back side access panel 20. The cleat 28 provides a storage mechanism for a hose, tube, cord or other item. As illustrated in FIG. 4, besides containers 26, a number of other dialysis items 30 can be stored within cavity 24. FIGS. 2 and 4 also illustrate that a power switch 32 is provided in an embodiment in a safe, out of the way location so that machine 10 is not inadvertently shut down during therapy.

The body 12 of machine 10 includes a number of additional cavities, aside from cavity 24, that aid in the attachment or configuration of various functional dialysis components. FIG. 4 for example illustrates a cavity 34 defined by upper back side access panel 22, which houses a number of cable connectors 36, such as electrical or hydraulic connectors. The cavity 34 enables the connectors 36 to be oriented downwardly so that a fluid spill onto the top 38 (FIG. 2) of the body 12 runs past and does not contact the connectors 36. The top 38 is flat and includes a rim 39 that collects spills made directly onto the top 38, for example, from bottles or containers placed on the top. FIGS. 2 and 4 also illustrate that the upper back side access panel 22 defines a number of air vents 40 for heat dissipation.

FIG. 2 also illustrates a number of cavities or facets 42 and 44 that facilitate the connection of tubes 46. Tubes 46 include, for example, the arterial and venus lines for hemodialysis and the catheter lines for peritoneal dialysis. Tubes 46 also include any other tubing necessary to perform a particular type of dialysis therapy. Cavities or facets 42 and 44 enable the connection of the tubes to the body 12 to be oriented in a desired direction. For example, cavity 42 enables the tubes 46 to extend downwardly from the cavity 42. The facet 44 provides a flat surface for a number of bulkhead type connections to the tubes 46.

FIGS. 1, 3, 4 and 5 illustrate a holder 45 extending from the body 12 of machine 10, above the right side access panel 16. Holder 45 is a bent metal or plastic structure in an embodiment. Holder 45 is useful for holding, supporting and storing a number of different dialysis items. Holder 45 is particularly useful for holding, supporting and/or storing a blood pressure cuff.

The figures each illustrate that the machine 10 rolls along rollers 48. Rollers 48 rotate about an axle. The axle connects to a post that rotatably attaches to a fixed portion of the machine 10. The post allows the rollers 48 to swivel and therefore turn as well as roll. The rollers 48 in an embodiment also include locking mechanisms as is well known in the art that allow the caregiver to lock one or more of the rollers 48 and thereby lock the machine 10 at a particular location. Rear rollers 48 connect directly to a portion of the body 12. Front rollers 48 in an embodiment connect to a base 50 that extends outwardly from the front side of the body 12. Placing rollers 48 on the base 50 provides a larger footprint for the rollers, which support the entire machine 10. This helps keep machine 10 from tipping when the caregiver pushes or pulls the combined display and handle 100 or the rear facing handle 14. Base 50 also defines a number of contours 52 that divert and channel any fluid that spills onto the base 50 to a desired location for cleaning. The channels 52 aid in the cleanup of spills made in the front of machine 10.

A clamp-like dialyzer holder 54 extends from the front of the body 12 as illustrated in FIGS. 1, 2, 3, 5 and 6. The dialyzer holder 54 provides a claw or clamp that allows for one handed insertion of a dialyzer for hemodialysis, or a filter, for hemofiltration, into the holder 54. The dialyzer holder 54 enables a dialyzer to be readily inserted and removed from the holder 54. Further, in some instances a dialyzer must be flipped, wherein holder 54 enables and facilitates the flipping of the dialyzer.

Dialyzer holder 54 also pivots and locks horizontally and outwardly approximately ninety degrees so as to extend from the left side access panel 18 of machine 10. If desired, holder 54 can be maintained in the sideways position or be maintained in the illustrated forward position, for example, when machine 10 is in narrow quarters. Dialyzer holder 54 includes one or more built-in tubing clips 56. Tubing clips 56 are plastic or metal and hold, support and/or store medical tubing, such as tubing running from the machine 10 to a dialyzer supported by holder 54.

A front panel 58 provides an interior space for mounting many of the components, fluidics and electronics used in machine 10. A number of lights, buttons, holders and other types of components are provided on the outside of front panel 58. The combination display and handle 100 sits above these components on the front of machine 10.

Combination display and handle 100 includes handle portions 102 that provide an open area where no control components reside, so that the caregiver, patient, nurse or other operator can grasp the display 100 at the portions 102 and move the entire machine 10 by rolling same via rollers 48. The shape of the display 100 includes forms and contours at the portions 102 that facilitate and serve as handles for grasping the display 100. Handle portions 102 and the display 100 enable the person to orientate the entire machine as opposed to unlocking a locking mechanism and moving the display relative to the body 12 of the machine 10. Moving the entire machine to see the display 100 can thereby be accomplished from any position relative to the machine and with a single hand.

Display 100 includes a video monitor 104, which in an embodiment operates in conjunction with a touch screen and a touch screen controller that communicates with the overall processor of the machine 10. Video monitor 104 displays various stages during the dialysis therapy, including for example the level of fluid in the patient's peritoneal cavity, in a fill or in a drain bag. Video monitor 104 also displays any other relevant dialysis parameters, such as fluid pressure, fluid flowrate, fluid temperature, whether or not one or more pumps is currently operating, or operating properly, as well as other parameters.

In the case where display 100 includes a touch screen, various inputs are made directly to the video monitor 104. Display 100 also includes one or more electromechanical inputs 106 that perform verification functions, scrolling functions, display adjustment functions or any other function that is desirably controlled by an electromechanical input. As illustrated perhaps most clearly by FIG. 2, display 100 includes a chart or document holder 112 that enables the operator to conveniently place charts, documents or other medical record information behind the display 100, where it is kept in a convenient place. The display/handle 100 also includes a device holder 108 (FIG. 3) for supporting a desired item, such as one or more blood tubing expansion chambers.

As illustrated most clearly by side views of FIGS. 5 and 6, the display 100 mounts directly to the body 12 via a sturdy and broad interface 110. Interface 110 bridges the distance between the display 100 and the body 12. Interface 10 does not extend far enough away from body 12 to cause cantilever effects as would be the case if interface 110 was thinner or longer. Interface 110 provides the stability and strength to allow a person to turn the entire machine 10 via the display 100 from the front of the machine or at odd angles with respect to the machine, such as lying next to the machine. As illustrated by FIGS. 5 and 6, the thickness T of the display/handle 100 is greater than the distance between the display 100 and the body 12. This also provides for a sturdy display 100, which can withstand the force of a person grasping and moving same.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A dialysis machine comprising:
a body supported by a plurality of rollers;
a plurality of tubes for transferring a fluid to and from a patient attached to the body; and
a mount for a display that displays and enables control of at least one dialysis function, the display mount fixedly attached to a front of the body and including a pair of handle portions for a person to grasp the display mount and roll the display and body collectively, the rollers spaced apart beneath the body a distance so that the body does not tip when an amount of force necessary to roll the body and the display is applied to the display mount.

2. The dialysis machine of claim 1, which includes a handle on the machine which extends towards a back of the machine so that a person in back of the machine can grab the handle and move the machine.

3. The dialysis machine of claim 1, wherein the display mount is constructed to withstand a grasping force applied by the person moving the machine.

4. The dialysis machine of claim 1, wherein the display comprises a touch screen monitor.

5. A dialysis machine, comprising:
a body;
a plurality of rollers mounted beneath the body;
a plurality of tubes for transferring a fluid to and from a patient attached to the body; and
a display mount fixedly mounted to a front of the body, and a display, the display enabling visualization and control of at least one dialysis function, wherein the display mount is configured so that a user can grasp the display mount with two hands and move the display mount and body together.

6. The dialysis machine according to claim 5, further comprising a bracket fixedly mounted to a rear of the display mount.

7. The dialysis machine according to claim 5, further comprising at least one dialyzer holder extending from the front of the body for supporting a dialysis component.

8. The dialysis machine according to claim 5, further comprising space for holding containers.

9. The dialysis machine according to claim 5, further comprising storage accessories mounted to the rear of the dialysis machine, the storage accessories configured to store a plurality of items for dialysis.

10. The dialysis machine according to claim 5, wherein the front of the machine is configured to drain away spills.

11. The dialysis machine according to claim 5, further comprising a plurality of fluid connectors downwardly mounted on a rear of the machine.

12. The dialysis machine according to claim 5, further comprising at least one holder on the front of the body for at least one of a cuff and a device.

13. A dialysis machine, comprising:
a body;
a plurality of rollers mounted beneath the body;
a handle fixedly mounted to a front of the body, the handle configured to fixedly mount a monitor;
a plurality of tubes for transferring a fluid to and from a patient attached to the body; and
a controller/monitor mounted within the handle and enabling visualization and control of at least one dialysis function, wherein the handle is configured so that a user can grasp the handle with both hands and move the display and body together.

14. The dialysis machine according to claim 13, wherein the front of the body further comprises multiple access panels to an interior of the body.

15. The dialysis machine according to claim 13, further comprising a back handle on the machine which extends towards a back of the machine configured so that a person in back of the machine can grab the back handle and move the machine.

16. The dialysis machine according to claim 13, further comprising an interface fixedly mounted between the body and the handle.

17. The dialysis machine according to claim 13, wherein the machine and the handle are configured for movement of the machine by a person lying next to the machine and maneuvering the machine via the handle.

18. The dialysis machine according to claim 13, further comprising an axle about which the rollers rotate and a post rotatably mounted to the dialysis machine and to the axle, wherein the rollers can rotate and swivel.

19. The dialysis machine according to claim 13, wherein the handle has an open area suitable for grasping by a hand of a user, wherein the machine can be positioned by a single hand.

20. The dialysis machine according to claim 13, wherein the handle is integrally attached to a front of the body.

* * * * *